United States Patent [19]

Kissinger

[11] Patent Number: 5,304,689

[45] Date of Patent: Apr. 19, 1994

[54] STABILIZATION OF COLOR IN PRODUCTION OF PARACUMYLPHENOL USING HYPOPHOSPHOROUS ACID

[75] Inventor: Gaylord M. Kissinger, Evansville, Ind.

[73] Assignee: General Electric Company, Pittsfield, Mass.

[21] Appl. No.: 42,976

[22] Filed: Apr. 5, 1993

Related U.S. Application Data

[63] Continuation-in-part of Ser. No. 891,025, Jun. 1, 1992, Pat. No. 5,185,475.

[51] Int. Cl.$^5$ .................... C07C 37/14; C07C 37/68; C07C 39/14
[52] U.S. Cl. .................... 568/748; 568/724; 568/744; 568/747
[58] Field of Search ............ 568/744, 748, 702, 724, 568/747

[56] References Cited

U.S. PATENT DOCUMENTS

| | | |
|---|---|---|
| 2,366,007 | 12/1944 | D'Alelio .................... 210/24 |
| 2,632,001 | 3/1953 | McMaster et al. .................... 260/88.1 |
| 3,037,052 | 5/1962 | Bortnick .................... 260/485 |
| 4,876,391 | 10/1989 | Kissinger .................... 568/724 |
| 4,902,836 | 2/1990 | Kissinger .................... 568/702 |
| 4,906,791 | 3/1990 | Imanari et al. .................... 568/744 |
| 5,185,475 | 2/1993 | Kissinger .................... 568/748 |

FOREIGN PATENT DOCUMENTS

| | | | |
|---|---|---|---|
| 0347835 | 12/1989 | European Pat. Off. .................... | 568/744 |
| 3922518 | 1/1991 | Fed. Rep. of Germany .................... | 568/744 |

OTHER PUBLICATIONS

U.S. patent application Ser. No. 07/891,025, filed Jun. 1, 1992, attorney docket No. 8CL-6982 Encyclopedia of Polymer Science and Technology, 1967, vol. 7, pp. 695-708, Third Edition, 1981.

Primary Examiner—Werren B. Lone

[57] ABSTRACT

Para-cumylphenol is continuously produced by the reaction of purified phenol and alpha-methylatyrene in the presence of an acidic catalyst and an effective amount of hypophosphorous acid ($H_3PO_2$) for stabilizing the color and UV absorption.

19 Claims, 1 Drawing Sheet

STABILIZATION OF COLOR IN PRODUCTION OF PARACUMYLPHENOL USING HYPOPHOSPHOROUS ACID

RELATED APPLICATION

This application is a continuation-in-part of copending U.S. patent application Ser. No. 07/891,025, filed Jun. 1, 1992, now U.S. Pat. No. 5,185,475.

BACKGROUND OF THE INVENTION

The invention relates to the continuous production of para-cumylphenol and, in particular, to the stabilization of color using hypophosphorous acid.

Para-cumylphenol is prepared by the reaction of purified phenol and alpha-methylstyrene in the presence of an acidic catalyst. During the process, the reaction effluent stream is stripped of the phenol solvent carrier in a stripper column and later subjected to nitrogen desorbing to remove residual phenol and other volatile impurities. Long residence times in the phenol stripping column and the nitrogen desorber have resulted in thermal/oxidative degradation of the para-cumylphenol product, leading to significant color formation which is undesirable.

SUMMARY OF THE INVENTION

The invention is based upon the discovery that hypophosphorous acid is effective to reduce or eliminate color in para-cumylphenol production. In a particular embodiment, the invention is directed to a method for continuous manufacture of a color stabilized para-cumylphenol comprising the step of reacting a stream containing purified phenol and alpha-methylstyrene in an acidic catalyst followed by removal of bulk phenol in a stripper column at elevated temperature and reduced pressure. Residual phenol is then desorbed within a packed column operating at elevated temperature and near atmospheric pressure. In the process, an effective amount of $H_3PO_2$ is added to the effluent stream for stabilizing the color of the para-cumylphenol product.

DESCRIPTION OF THE INVENTION

Figure 1:
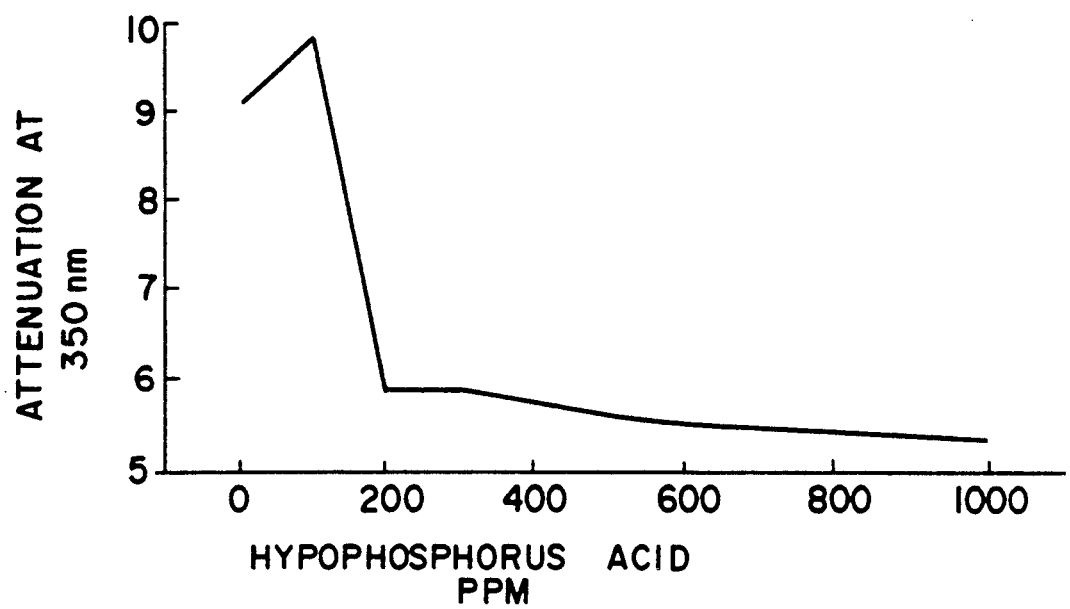
FIG. 1 is a graphical representation of the effect of added hypophosphorous acid on the UV absorption in the production of para-cumylphenol.

Para-cumylphenol is continuously produced by the reaction of feed stream of purified phenol (e.g. 99.5%) and alpha-methylstyrene in the presence of an acidic catalyst, such as HCl or an ion exchange catalyst bed. Bulk phenol is removed in a stripper column operated at elevated temperature and reduced pressure (e.g. about 346° F. and about 135 mmhg absolute). Thereafter, residual phenol and some light boiling impurities are removed from the stream in a packed column using nitrogen as a desorbing agent at elevated temperature (e.g. about 365° F.) and near atmospheric pressure.

The related U.S. patent application Ser. No. 07/891,025, filed Jun. 1, 1992, incorporated herein by reference, sets forth in detail a process for the preparation of paracumylphenol. The method comprises reacting alpha-methylstyrene (AMS) with a purity greater than about 99.0 wt. % with a molecular excess of phenol having a purity greater than about 99.90 wt. % in the contact presence of a solid organic cation exchange resin at a temperature of from about 40° C. to about 100° C. and obtaining a stream containing para-cumylphenol, phenol and small quantities of side reaction byproducts comprising ortho-cumylphenol and alpha-methylstyrene dimers, removing excess phenol and other unwanted materials which are lower boiling than paracumylphenol, thereby leaving a stream which is at least about 98 wt. % para-cumylphenol.

In the invention, an effective amount of hypophosphorous acid ($H_3PO_2$) is added to the effluent stream for stabilizing or eliminating the color of the para-cumylphenol product. Generally, the amount of $H_3PO_2$ ranges from about 10 to about 2,000 ppm addition level and preferably from about 50 to about 1000 ppm addition level.

The alpha-methylstyrene employed should have a weight percent purity above about 99.0 wt. %, preferably above about 99.5 wt. %. The phenol employed as the reactant should be above about 99.95 wt. % purity. Such alpha-methylstyrene and phenol are readily obtained as a side product and the main product from a process starting from cumene. The phenol can be the direct product of such process or obtained from market sources and the alpha-methylstyrene can be obtained from market sources. The alpha-methylstyrene and phenol are contacted in quantities wherein there is a substantial excess of phenol. Generally an excess as measured in moles of from about 3 times to about 15 times excess phenol to AMS can be employed. These streams are passed over an acid catalyst system. Although any acid catalyst system (e.g., HCl) can be employed it is much preferred to employ a solid acid catalyst system so that there are no unnecessary separation steps of one liquid from another or acid recovery steps. Such acid catalyst systems are commonly present as organic acid catalyst systems such as the sulfonic acid cation exchange resins manufactured by various companies. Examples of acidic ion exchange resins useful in catalyzing this reaction are generally well known compositions as are methods of their preparation, see for example the preparative procedures described in U.S. Pat. No. 3,037,052 which is hereby incorporated herein by reference thereto. Representative of acid ion-exchange resins are strong-acid ion exchangers, such as those resins or polymers having a plurality of pendant sulfonic acid groups. Examples include sulfonated polystyrene or poly(styrenedivinylbenzene) copolymer and sulfonated phenolformaldehyde resins. The sulfonated resins are commercially available in water swollen form as gellular and macro-reticular types. Specific examples of commercially available candidate resins are Amberlite IR-120H, Amberlyst Amberlyst 31, Dowex 50-X-4, Dowex MSC-1H, Duolite c-291 (Amberlite, Amberlyst, Dowex, Duolite, Permutit, Chempro and Imac are registered U.S. trademarks). Further examples of such ion exchangers as well as methods f or preparing such ion exchangers are described in the *Encyclopedia of Polymer Science and Technology*, 1967, vol. 7, pages 695 to 708 and third edition, 1981. The exchange capacity of the acidic resin is preferably at least 2.0 meq. $H+/g$ of dry resin, with exchange capacities in the range of from 3.0 to 5.5 meg. $H+/g$ (dry resin) particularly preferred. Preferred catalyst are the Amberlyst ® gellular types, which are styrene cross-linked with divinlybenzene or like cross-linking monomer and having pendant sulfonic acid groups attached to the aromatic nucleus of the styrene moiety. Sulfonation may be by the process described in U.S. Pat. No. 2,366,007 which is incorporated herein by reference thereto. See also U.S. Pat. Nos. 4,902,836 and 4,876,391 incorporated herein by reference.

Preferred catalyst systems include a cation exchange resin such as Rohm and Haas XE-364. This resin is a sulfonated polystyrene. Either a single reactor or multiple reactors in series can be used. However the feed rate as measured in weighted hourly space velocity (WHSV) can vary between from about 0.1 to 12.0 pounds feed/hr. per pound dry catalyst. Preferred is about 0.2 to 6.0. Of course, the feed rate determines the residence time of the feed materials in contact with the catalyst and therefore helps to determine the conversion and selectivity in the actual reaction. Usually most reactions are a compromise between conversion and selectivity. The longer the residence time the greater the conversion; however, the lower the selectivity. Temperatures of the reactor are from abut 40° to about 100° C., again having the expected impact on productivity and selectivity of the reaction step.

Generally the exiting stream from the reactor or series of reactors has had 100% of the AMS converted to a product. This product is very rich in paracumylphenol. There is a small amount of orthocumylphenol, dimers of AMS and other usually unknown side products. This stream is then preferably contacted with a material which is anionic and which neutralizes or renders ineffective for catalyzing any future side reactions materials from the cation exchange resin which are leached out or removed by the stream contacting the catalyst. Such anionic materials can be weak basic or weak salts which can bring about the neutralization of any material leached from the catalyst such as oligomers bearing the cationic group. Examples of such weak bases include the carbonates such as barium carbonate, magnesium carbonate and manganese carbonate. However because of the potential separation problems present with such materials, it is better to use a solid anion exchange resin to bring about such effect.

The ion exchange resins useful in the method of this invention include all known basic resins of this type. For the most part, they are amine or quaternary ammonium resins typically containing such moieties as dimethylbenzylamino groups or corresponding methylquaternized groups attached to a polymer chain. Amine resins including those having a pyridyl group are often preferred. For the purpose of the invention, the amine resins are employed in the free base form, although quaternary resins wherein the counterion therein is a hydroxide anion can also be used.

Methods of preparing anionic exchange resins are generally well known; see for example the method described in U.S. Pat. No. 2,632,001 (McMasters et al.) incorporated herein by reference thereto. This method comprises the side-chain chlorination of poly(vinyltoluene), followed by reaction with a tertiary amine in the presence of a polar solvent such as water to form a quaternary ammonium salt. Representative of commercially available resins of this type are Amberlite IRA-400, Amberlite IRA-401, Amberlite IRA-402, Amberlite IRA-900, Duolite A-101-D. Duolite ES-111, Dowex 1, Dowex 11, Dowex 21K, and Ionac A-540 and those derived from dimethylethanolamine $(CH_3)_2-NCH_2CH_2OH$, Amberlite IRA-410, Amberlite IRA-911, Dowex 2, Duolite A-102-D, Ionac A-542, and Ionac A-550 (Amberlite, Duolite, Dowex and Ionac are registered U.S. trademarks).

Weak-base anionic exchange resins, containing primary, secondary and tertiary amine groups are preferred for use in the present invention. Examples of commercially available candidate products for weakbase anionic exchange resins are Amberlite A-21, Dowex 44, Duolite A-7, Ionac A-260, Amberlite IRA-35, Amberlite IRA-68 (the latter two resins are gellular with acrylic backbones) and Reillex-402, a polyvinyl pyridine from Reilly Industries, Inc.

Contact between the para-cumylphenol stream in the anion exchange resin may be effected by any convenient means. Generally, the stream passes through the resin at temperatures in a range which is similar to that wherein the conversion of the phenol to the paracumylphenol occurs. Generally such temperature is from about 40° to about 120° C. preferably from about 50° to 75° C. Passage of the phenol mixture through the resin may be upward or downward, for time sufficient to remove any contaminants which may be present. As in the acidic cation exchange resin utilized in the first step, such anion exchange resin may be used until it has been exhausted. Standard regeneration procedures may be used for either the cation exchange or the anion exchange resins employed in this process.

As noted before there is a substantial amount of excess phenol present in the reaction. All of this phenol has been carried along through the past processing. This excess phenol is now removed. The phenol can be removed by standard processing such as distillation since its boiling point is significantly different than the para-cumylphenol and many other side products and impurities present. Generally such separation occurs in a stripping type column at a reduced pressure and a relatively low temperature utilizing standard operational apparatuses. Residual phenol is removed in the presence of a non reactive gas and surface enhancer such as packing in a column. Examples of such a gas are nitrogen and carbon dioxide, preferably nitrogen. Depending upon the yields required as well as the purity as measured by weight percent and the quality of the desired para-cumylphenol as measured for example by color, all of these procedures can be used to remove various percentages of the phenol or only one procedure can be employed.

Generally, an appropriate balance of the processing conditions can bring about at least 97 to 98 wt. % pure para-cumylphenol with low amounts of AMS dimers, ortho-cumylphenol and other materials. The precise composition analysis will vary depending upon the particular operating conditions. Generally the product has an APHA color of 5 or less units in a 10% para-cumylphenol in methanol solution. However all of these quantities can vary somewhat dependent upon the conditions of reaction in the phenol removal.

In accordance with the invention, the color of the para-cumylphenol product can be significantly improved by the addition of certain additives for example hypophosphorous acid. Such addition can occur anywhere in the actual process and in fact can be used to a particular advantage when the para-cumylphenol melt need be held in storage. The actual addition point in the process can be in the streams contacting the cation exchange resin, however, it is preferred to add such color stabilizing additive after the contacting of the product stream with the anionic material, when it is employed.

For process economics it is quite clear that the phenol which has been removed can be recycled to the reactor. It should also be noted that isomers of paracumylphenol which traveled together with the removed phenol can also be present and contact the cation exchange catalyst once more in the presence of new phenol and AMS. Such cation exchange resin has the ability to rearrange certain byproducts to the desired para-cumylphenol.

The following examples illustrate the teaching of the invention but should not be construed as a limitation thereof.

EXAMPLE

A low purity para-cumylphenol was chosen to critically examine the potential effects a stabilizer might have in reducing color. The characterization in weight percent of this para-cumylphenol, hereinafter called the starting material, was as follows:

| p-cp | o-cp | AMS Dimers | Unknowns | APHA | Absorbance |
|------|------|------------|----------|------|------------|
| 94.84% | 3.18% | 1.52% | 0.46% | 25 | 3.4 | p-cp = para-cumylphenol
o-cp = ortho-cumylphenol
AMS Dimers = linear and cyclic dimers of alpha-methylstyrene
Unknowns = miscellaneous compounds, including some p,p'-bisphenol and o,p'-bisphenol.
APHA = American Public Health Association (APHA) test for yellowness, measured as a solution of para-cumylphenol in methanol, compared to Cobalt Color Standards.
Absorbance = attenuation measured at 350 nm of a 10% solution of para-cumylphenol dissolved in methanol.

The starting material was divided into 25 gram portions, each of which was charged into glass test tubes, and placed in a heating block set at 185° C. These tests were carried out for a total heating time of 6 hours.

The results were consistently the same over several experimental sets. The starting material was placed in tube 1 with no additives as a control. $H_3PO_2$ was added in increasing amounts to tubes 2–6. The contents of all the tubes were analyzed upon completion of the 6 hours heating period. The results were as follows:

| Tube | $H_3PO_2$ ppm | p-cp | o-cp | AMS Dimers | Unknowns | APHA | Absorption |
|------|------|------|------|------|------|------|------|
| 1 | 0 | 95.03% | 2.83% | 1.55% | 0.59% | 250 | 8.92 |
| 2 | 100 | 94.90% | 3.04% | 1.56% | 0.50% | 72 | 9.88 |
| 3 | 300 | — | — | — | — | 36 | 5.87 |
| 4 | 500 | 95.07% | 2.80% | 1.59% | 0.54% | 29 | 5.57 |
| 5 | 1000 | 95.26% | 2.88% | 1.35% | 0.59% | 23 | 5.44 |
| 6 | 2000 | 95.14% | 2.83% | 1.47% | 0.56% | 20 | 6.44 |

Figure 2:
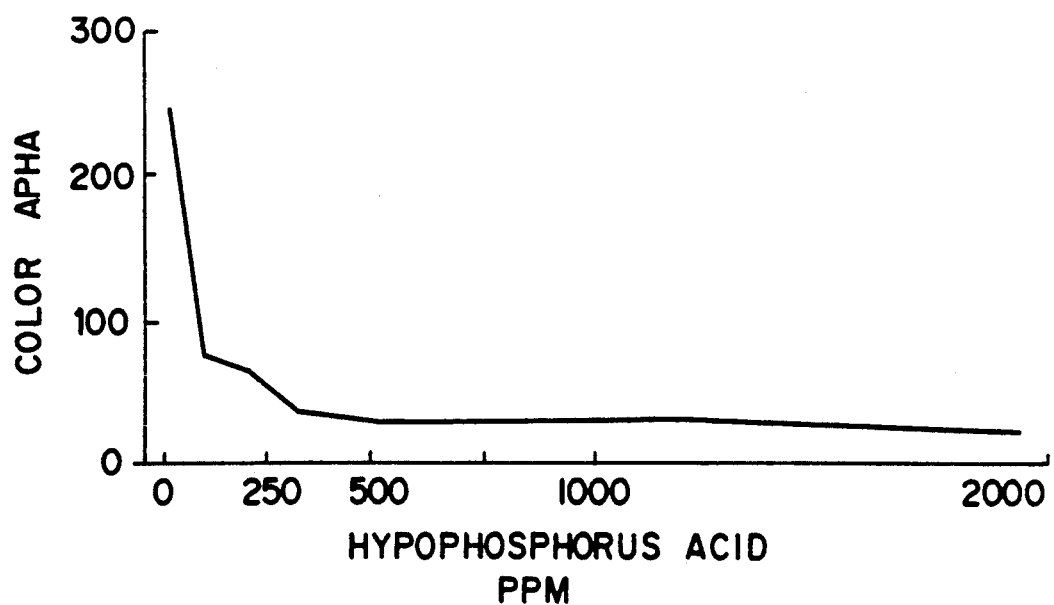
FIG. 2 is a graphical representation of the effect of hypophosphorous acid on the APHA color in the production of para-cumylphenol.

As one can see from the data above, the effect of $H_3PO_2$ on reducing color is dramatic. Attached, FIG. 1 shows the data for absorption plotted in graphic form, and FIG. 2 shows the APHA data in graphical form. Absorption is a measure of the decrease in the intensity of 350 nm radiation through a 10 cm sample of 10% solution of para-cumylphenol relative to pure methanol.

In the continuous process for making paracumylphenol, an effluent stream of purified phenol and alpha-methylstyrene are reacted in an acidic catalyst or a fixed ion exchange catalyst bed. Exemplary catalysts include acidic materials, e.g. HCl and ion exchange resins such as Mobay Lewatit or Rohm & Haas XE-561 (2% crosslinked) or XE-364 (4% crosslinked). The stabilizer $H_3PO_2$ is added to the effluent stream at the reactor output. After formation of the product, bulk phenol removal follows in a stripper column, operating at 346° F., and 135 mm Hg absolute heated, for example, by means of a circulation reboiler. Following stripping, residual phenol and some of the light boiling impurities are removed from the effluent stream in a packed column using a heated inert gas, e.g. nitrogen, as a desorbing agent. This step is carried out at atmospheric pressure, and at a temperature of 365° F. These process steps, along with the $H_3PO_2$ stabilizer at between 10 and 2000 ppm addition level, results in a para-cumylphenol product of excellent color and quality.

While there has been described what at present are considered to be the preferred embodiments of the present invention, it will be readily apparent to those skilled in the art that various changes and modifications may be made therein without departing from the invention and it is intended in the appended claims to cover such changes and modifications as fall within the true spirit and scope of the invention.

What is claimed:

1. A continuous process for manufacturing paracumylphenol comprising the steps of:
    reacting a stream of a purified phenol and alpha-methylstyrene in the presence of an acidic catalyst to form a first effluent stream;
    adding an effective amount of hypophosphorous acid to the effluent stream for stabilizing color of the para-cumylphenol product;
    stripping bulk phenol from the effluent stream in a stripper column operating at a selected temperature and pressure; and
    desorbing residual phenol in the effluent stream in a desorbing column employing an inert gas as a desorbing agent.

2. The method according to claim 1, wherein the hypophosphorous acid is added in an amount ranging from about 10 to about 2,000 parts per million addition.

3. The method to claim 1, wherein the hypophosphorous acid is added in an amount ranging from about 50 to about 100 million addition.

4. The method according to claim 1, wherein the stripper operates at about 346° F. and about 135 Mm hg absolute.

5. The method according to claim 1, wherein said desorbing agent comprises nitrogen.

6. The method according to claim 1, wherein the desorber column operates at about 365° F. and about atmospheric pressure.

7. The method according to claim 1, further comprising the step of recycling phenol and byproducts to the stream for further reaction with catalyst resin.

8. The method according to claim 1, wherein the product has a color less than about 250 APHA.

9. The method according to claim 1, wherein the product has an absorption at 350 nm less than about 9 through a 10 cm sample 10% solution of para-cumylphenol in methanol.

10. The method according to claim 1, wherein the phenol is about 99.5% pure.

11. The method according to claim 1, wherein the catalyst comprises a material selected from the group consisting of HCl, and ion exchange resins.

12. The method according to claim 1, wherein said catalyst comprises a sulfonated ion exchange resin having a polystyrene backbone.

13. The method according to claim 1, wherein the ion exchange resin is at least about 2% crosslinked.

14. The method according to claim 10, wherein the ion exchange resin is at least about 4% crosslinked.

15. The method according to claim 1, wherein the catalyst is immobilized.

16. A method for preparing para-cumylphenol in a highly selective manner comprising the steps of: reacting alpha-methylstyrene with a purity greater than about 99.5 wt. % with a molecular excess of phenol having a purity greater than about 99.95 wt. % in the contact presence of a solid organic cation exchange resin at a temperature of from about 40° C. to about 100° C. and obtaining a stream containing paracumylphenol, phenol and small quantities of side reaction products comprising ortho-cumylphenol and alpha-methylstyrene dimers;

adding an effective amount of hypophosphorous acid to the reaction product for stabilizing the color of the product; and removing excess phenol and other unwanted materials which are lower boiling than para-cumylphenol, thereby leaving a stream which is at least about 98 wt. % paracumylphenol.

17. The method in accordance with claim 16, wherein prior to removing excess phenol, the reaction product is contacted with an anion so as to neutralize cation which may be present.

18. The method in accordance with claim 16, wherein the hypophosphorous acid is added after the cation exchange resin.

19. The method in accordance with claim 16, wherein the hypophosphorous acid is added after the anion exchange resin bed.

* * * * *